(12) United States Patent
Ludviksson et al.

(10) Patent No.: US 7,064,812 B2
(45) Date of Patent: Jun. 20, 2006

(54) METHOD OF USING A SENSOR GAS TO DETERMINE EROSION LEVEL OF CONSUMABLE SYSTEM COMPONENTS

(75) Inventors: Audunn Ludviksson, Scottsdale, AZ (US); Steven T. Fink, Mesa, AZ (US)

(73) Assignee: Tokyo Electron Limited, Tokyo (JP)

( * ) Notice: Subject to any disclaimer, the term of this patent is extended or adjusted under 35 U.S.C. 154(b) by 322 days.

(21) Appl. No.: 10/642,621

(22) Filed: Aug. 19, 2003

(65) Prior Publication Data

US 2005/0041238 A1 Feb. 24, 2005

(51) Int. Cl.
*G01N 21/00* (2006.01)

(52) U.S. Cl. .......................... 356/72; 356/316; 250/282
(58) Field of Classification Search ................. 356/72, 356/316; 250/282
See application file for complete search history.

(56) References Cited

U.S. PATENT DOCUMENTS

| 5,146,098 | A | * | 9/1992 | Stack ...................... 250/492.2 |
| 5,187,542 | A | * | 2/1993 | Madzsar ..................... 356/311 |
| 5,712,702 | A | * | 1/1998 | McGahay et al. .......... 356/311 |
| 5,798,016 | A | * | 8/1998 | Oehrlein et al. ....... 156/345.37 |
| 5,947,053 | A | * | 9/1999 | Burnham et al. ....... 250/396 R |

* cited by examiner

*Primary Examiner*—Gregory J. Toatley, Jr.
*Assistant Examiner*—Kara Geisel
(74) *Attorney, Agent, or Firm*—Oblon, Spivak, McClelland, Maier & Neustadt, P.C.

(57) ABSTRACT

A method and system are provided for monitoring erosion of system components in a plasma processing system. The system components contain a gas emitter that can release a sensor gas into a plasma process environment. The sensor gas can produce characteristic fluorescent light emission when exposed to a plasma. The method can evaluate erosion of system components in a plasma, by monitoring fluorescent light emission and a mass signal from the sensor gas. Consumable system components that can be monitored using the method include rings, shields, electrodes, baffles, and liners.

51 Claims, 16 Drawing Sheets

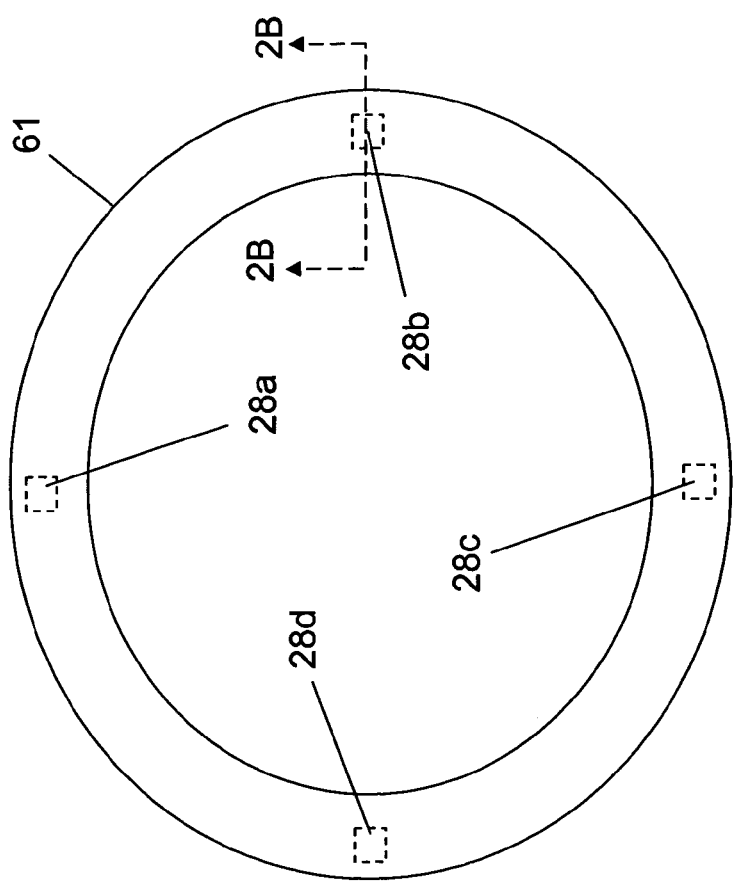
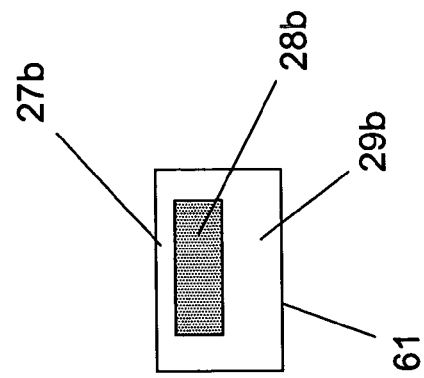
FIG. 2A
FIG. 2B

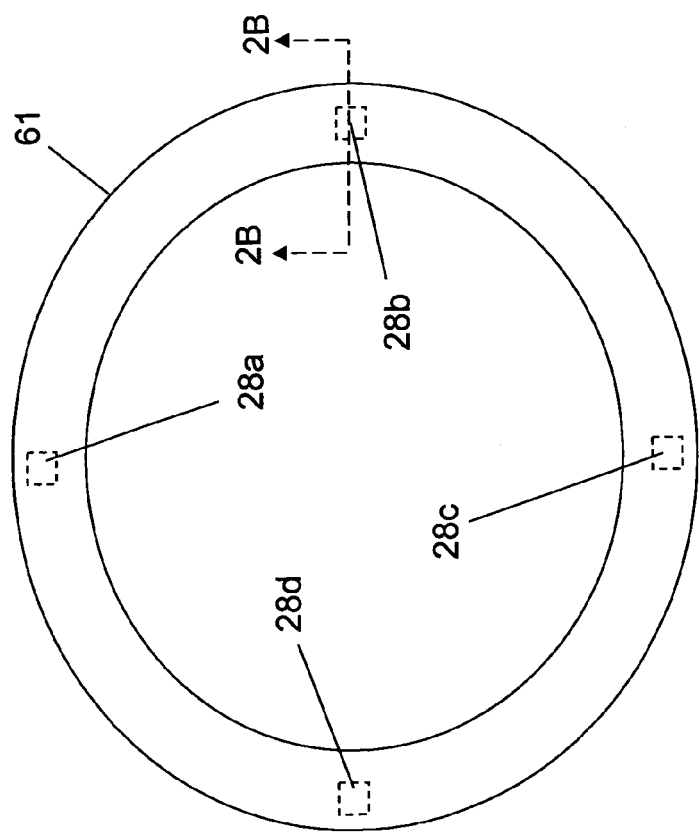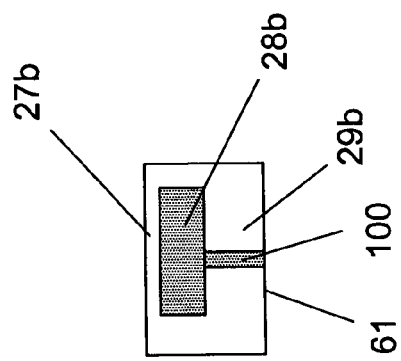
FIG. 3A
FIG. 3B

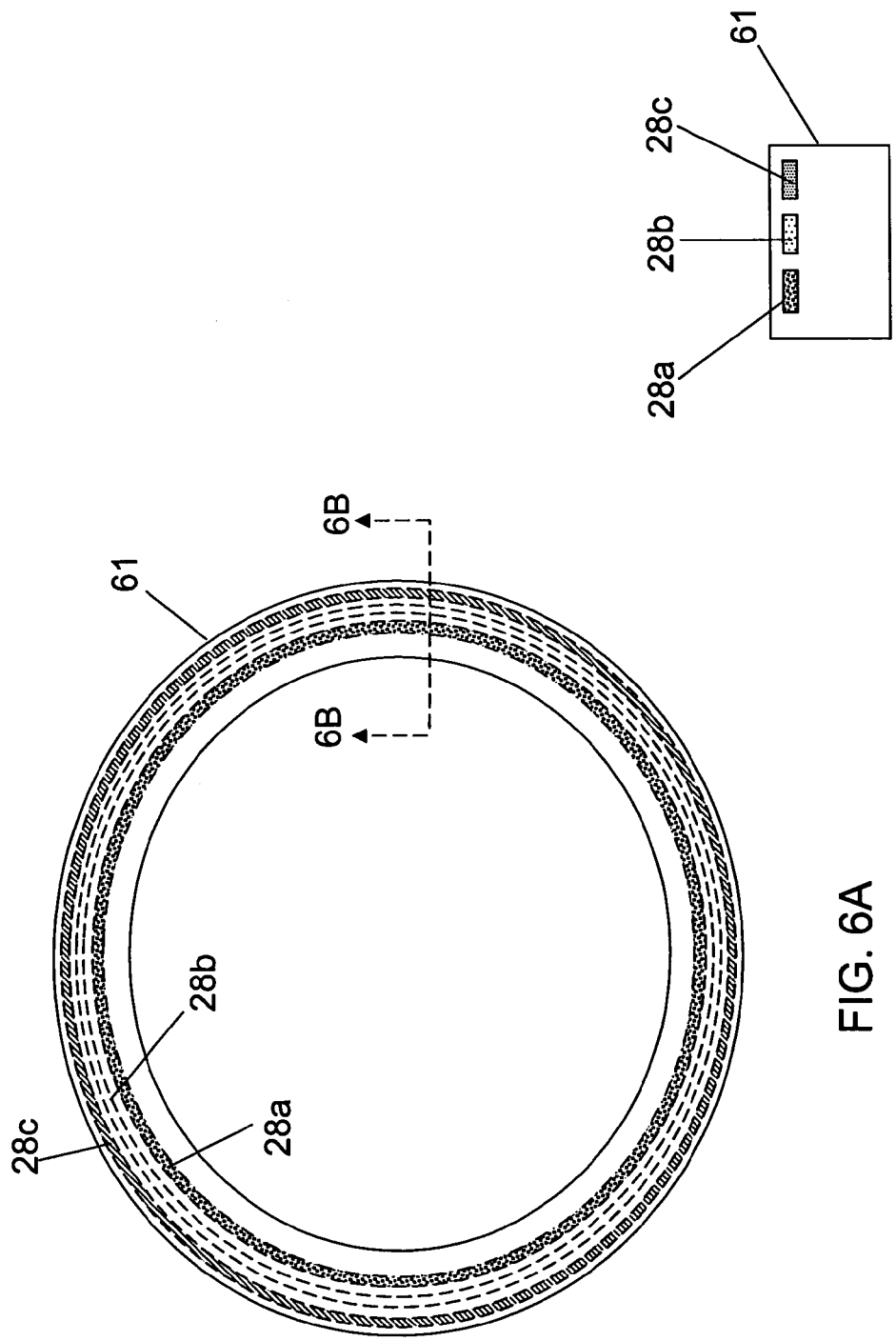

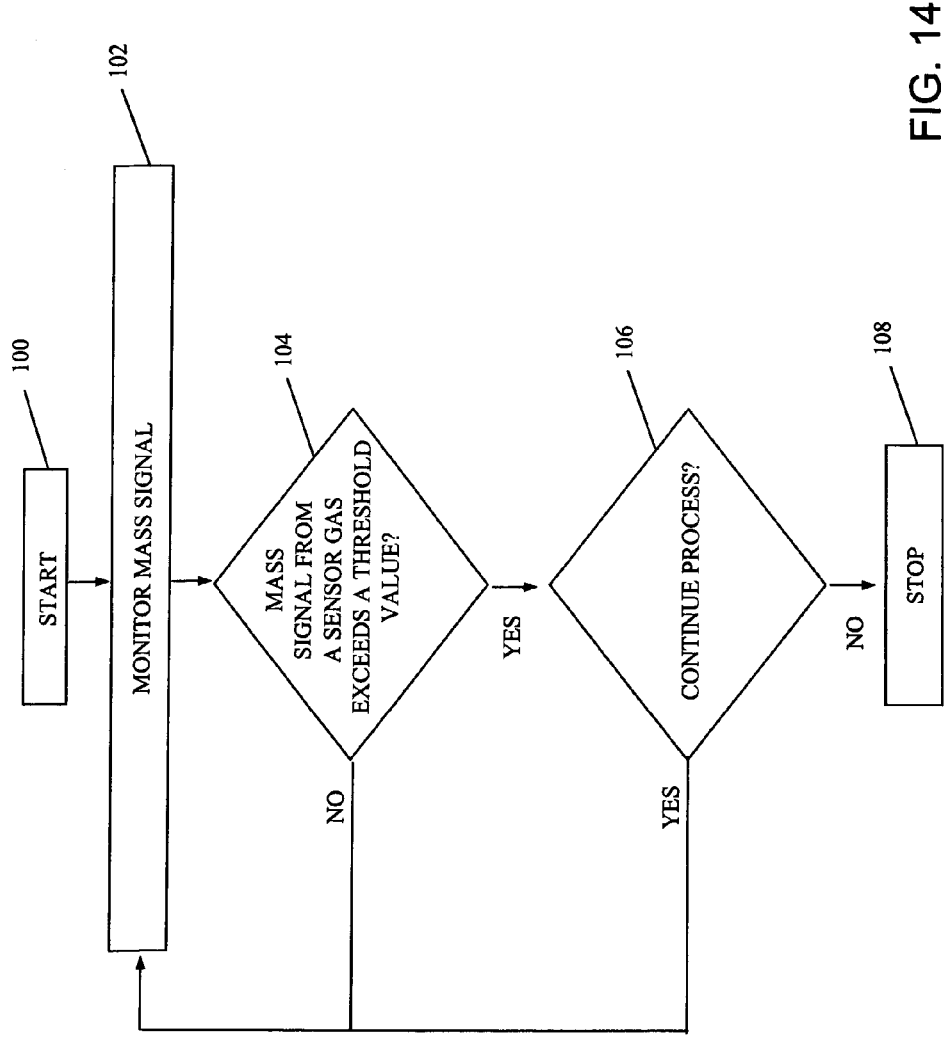

METHOD OF USING A SENSOR GAS TO DETERMINE EROSION LEVEL OF CONSUMABLE SYSTEM COMPONENTS

CROSS REFERENCE TO RELATED APPLICATIONS

The present invention is related to U.S. patent application Ser. No. 10/331,587, filed Dec. 31, 2002; and U.S. patent application Ser. No. 10/331,456, filed Dec. 31, 2002; the entire contents of which are herein incorporated by reference.

FIELD OF THE INVENTION

The present invention relates to semiconductor processing and more particularly to using a sensor gas to determine the erosion level of consumable system components in a plasma processing system.

BACKGROUND OF THE INVENTION

The fabrication of integrated circuits (IC) in the semiconductor industry typically employs plasma to create and assist surface chemistry within a plasma reactor necessary to remove material from and deposit material to a substrate. In general, plasma is formed within the plasma reactor under vacuum conditions by heating electrons to energies sufficient to sustain ionizing collisions with a supplied process gas. Moreover, the heated electrons can have energy sufficient to sustain dissociative collisions and, therefore, a specific set of gases under predetermined conditions (e.g., chamber pressure, gas flow rate, etc.) are chosen to produce a population of charged species and chemically reactive species suitable to the particular process being performed within the chamber (e.g., etching processes where materials are removed from the substrate or deposition processes where materials are added to the substrate).

Although the formation of a population of charged species (ions, etc.) and chemically reactive species is necessary for performing the function of the plasma processing system (i.e. material etch, material deposition, etc.) at the substrate surface, other component surfaces on the interior of the processing chamber are exposed to the physically and chemically active plasma and, in time, can erode or become coated with deposits. The erosion or coating of exposed system components in the plasma processing system can lead to a gradual degradation of the plasma processing performance and ultimately to complete failure of the system.

Various parts of a plasma processing system consist of consumable or replaceable components, that are fabricated from silicon, quartz, alumina, carbon, or silicon carbide, for example. Examples of consumable system components include electrodes, shields, rings, baffles, and liners. The consumable nature of the replaceable components can require frequent maintenance of the plasma processing system. This frequent maintenance can produce costs associated with plasma processing down-time and new plasma processing chamber components, which can be excessive.

Consumable parts are commonly replaced after detrimental processing conditions or processing results are observed. These adverse processing conditions can include plasma arcing, particle formation, variations in substrate etch rate, etch selectivity, and etch uniformity. Alternatively, consumable parts can be cleaned or replaced according to a predetermined maintenance schedule that can, for example, be based on the number of plasma operating hours. These methods can result in overdue or premature replacement of consumable system components.

SUMMARY OF THE INVENTION

A plasma processing system is provided that allows for monitoring erosion of system components during processing. The processing system comprises a processing chamber with system components that contain at least one gas emitter capable of releasing a sensor gas, and a monitoring system for monitoring release of the sensor gas into the processing environment. The monitoring system can comprise a mass sensor capable of monitoring a sensor gas or an optical monitoring system capable of monitoring fluorescent light emission when a sensor gas is exposed to a plasma.

A method is provided for monitoring erosion of a system component in a plasma processing system by exposing a system component containing gas emitter to a process, and monitoring a release of a sensor gas from the gas emitter during a process to determine erosion of the system component. The sensor gas can produce a characteristic fluorescent light emission when released into the process environment and exposed to a plasma. The method can utilize an optical monitoring system to monitor the fluorescent light emission. The release of the sensor gas can also be monitored by a mass sensor.

Monitorable consumable system components are provided that can contain at least one sensor gas that allows monitoring erosion of the consumable system components. The sensor gas can allow for characteristic fluorescent light emission when released and exposed to a plasma.

BRIEF DESCRIPTION OF THE DRAWINGS

The accompanying drawings, which are incorporated in and constitute a part of the specification, embodiments of the invention, and together with the general description given above and the detailed description of the embodiments given below, serve to explain the principles of the invention wherein:

FIG. 2A shows a plan view of a system component containing a plurality of gas emitters;

FIG. 2B shows a cross-sectional view of the system component in FIG. 2A;

FIG. 3A shows a plan view of a system component containing a plurality of gas emitters;

FIG. 3B shows a cross-sectional view of the system component in FIG. 3A;

FIG. 6A shows a plan view of a system component containing a plurality of gas emitters;

FIG. 6B shows a cross-sectional view of the system component in FIG. 6A;

FIG. 14 is a flowchart for monitoring the status of system components using a mass sensor.

DETAILED DESCRIPTION OF THE INVENTION

Figure 1:
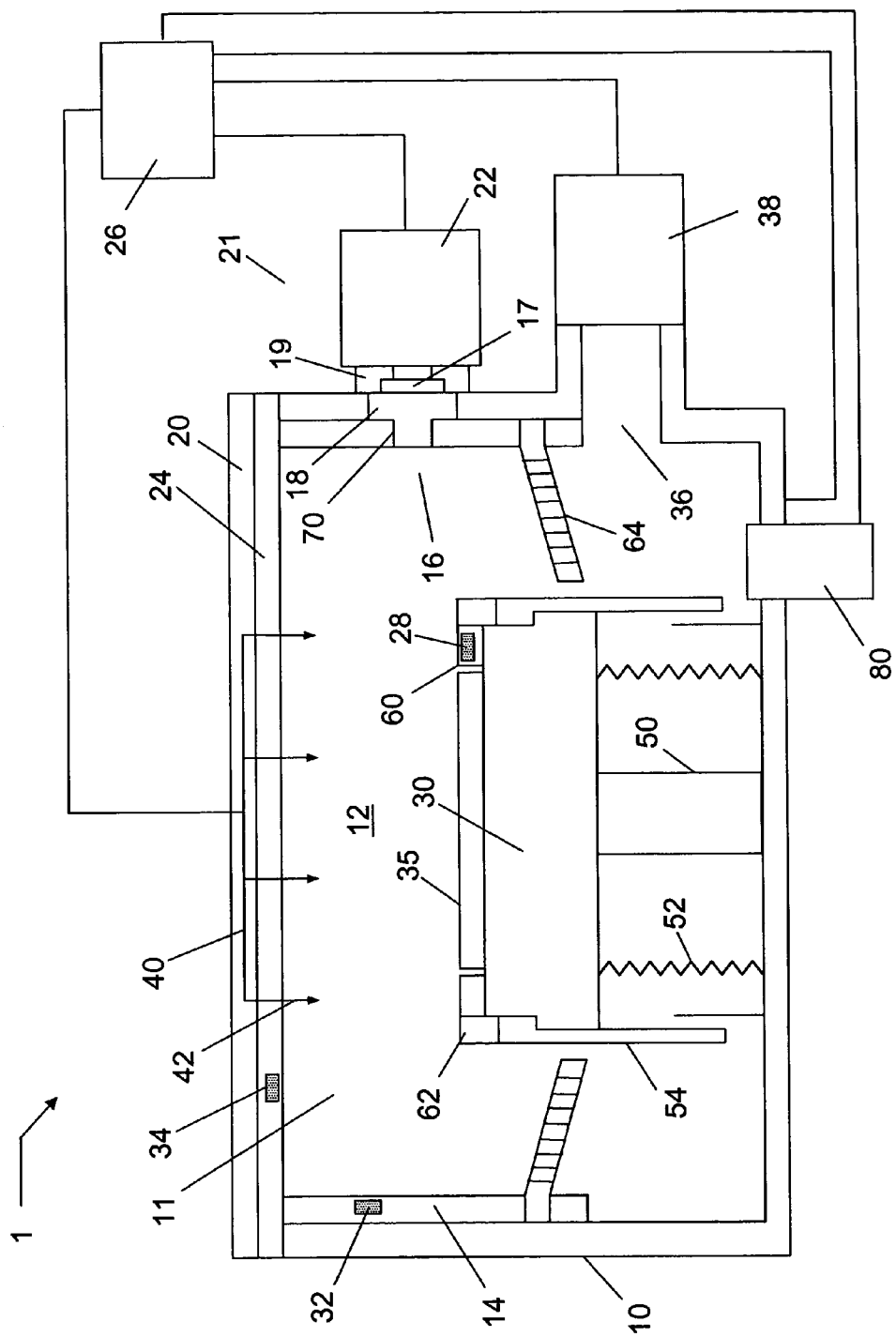
FIG. 1 shows a simplified block diagram of a plasma processing system.

FIG. 1 shows a simplified block diagram of a plasma processing system. A plasma processing system 1 is depicted in FIG. 1 comprising a plasma processing chamber 10, an upper assembly 20, an electrode plate 24, a substrate holder 30 for supporting a substrate 35, and a pumping duct 36 coupled to a vacuum pump 38 for providing a reduced pressure atmosphere 11 in plasma processing chamber 10. Plasma processing chamber 10 can facilitate the formation of a processing plasma in a process space 12 adjacent substrate 35. The plasma processing system 1 can be configured to process various substrates (i.e. 200 mm substrates, 300 mm substrates, or larger).

A gas injection assembly 40 can introduce process gas 42 to the plasma processing chamber 10. The gas injection system 40 can include a showerhead, wherein the process gas 42 is supplied from a gas delivery system (not shown) to the process space 12 through a gas injection plenum (not shown), a series of baffle plates (not shown) and a multi-orifice showerhead gas injection plate (not shown).

For example, an electrode plate 24 can be coupled to an RF source (not shown), and facilitate an upper electrode for the plasma processing system 1. In an alternate embodiment, the upper assembly 20 comprises a cover and an electrode plate 24, wherein the electrode plate 24 is maintained at an electrical potential equivalent to that of the plasma processing chamber 10. For example, the plasma processing chamber 10, the upper assembly 20, and the electrode plate 24 can be electrically connected to ground potential, and facilitate an upper electrode for the plasma processing system 1.

Plasma processing chamber 10 can, for example, further comprise a shield 14 and chamber liners (not shown) for protecting the plasma processing chamber 10 from the processing plasma in the process space 12, and an optical viewport 16. Optical viewport 16 can comprise an optical window 17 coupled to the backside of an optical window deposition shield 18, and an optical window flange 19 can be configured to couple optical window 17 to the optical window deposition shield 18. Sealing members (not shown), such as O-rings, can be provided between the optical window flange 19 and the optical window 17, between the optical window 17 and the optical window deposition shield 18, and between the optical window deposition shield 18 and the plasma processing chamber 10. Optical window deposition shield 18 can extend through an opening 70 within shield 14. Optical monitoring system 21 can permit monitoring of optical emission from the processing plasma in process space 12 using optical viewport 16 and optical diagnostic sensor 22.

A spectrometer (not shown) can be incorporated in the optical diagnostic sensor 22 to detect a plasma process condition based on an optical emission, e.g., light, from the process space 12. The spectrometer or the detector system can be associated with a photomultiplier tube, a CCD or other solid state detector to at least partially detect a plasma process condition, such as an endpoint of a plasma process, or status of a system component, for example. However, other optical devices capable of analyzing optical emission, can be used as well.

Substrate holder 30 can, for example, further comprise a vertical translational device 50 surrounded by a bellows 52 coupled to the substrate holder 30 and the plasma processing chamber 10, and configured to seal the vertical translational device 50 from the reduced pressure atmosphere 11 in plasma processing chamber 10. Additionally, a bellows shield 54 can, for example, be coupled to the substrate holder 30 and configured to protect the bellows 52 from the processing plasma. Substrate holder 30 can, for example, further be coupled to at least one of a focus ring 60, and a shield ring 62. Furthermore, a baffle plate 64 can extend about a periphery of the substrate holder 30.

Substrate 35 can be transferred into and out of plasma processing chamber 10 through a slot valve (not shown) and chamber feed-through (not shown) via robotic substrate transfer system where it is received by substrate lift pins (not shown) housed within substrate holder 30 and mechanically translated by devices housed therein. Once substrate 35 is received from substrate transfer system, it is lowered to an upper surface of substrate holder 30.

Substrate 35 can be affixed to the substrate holder 30 via an electrostatic clamping system. Furthermore, substrate holder 30 can, for example, further include a cooling system including a re-circulating coolant flow that receives heat from substrate holder 30 and transfers heat to a heat exchanger system (not shown), or when heating, transfers heat from the heat exchanger system. Moreover, gas can, for example, be delivered to the back-side of substrate 35 via a backside gas system to improve the gas-gap thermal conductance between substrate 35 and substrate holder 30. Such a system can be utilized when temperature control of the substrate is required at elevated or reduced temperatures. In other embodiments, heating elements, such as resistive heating elements, or thermo-electric heaters/coolers can be included.

In FIG. 1, substrate holder 30 can comprise an electrode through which RF power is coupled to the processing plasma in process space 12. For example, substrate holder 30 can be electrically biased at a RF voltage via the transmission of RF power from a RF generator (not shown) through an impedance match network (not shown) to substrate holder 30. The RF bias can serve to heat electrons to form and maintain plasma. In this configuration, the system can operate as a reactive ion etch (RIE) reactor, wherein the chamber and upper gas injection electrode serve as ground surfaces. A typical frequency for the RF bias can range from 1 MHz to 100 MHz. For example, plasma processing systems operating at 13.56 MHz are well known to those skilled in the art.

The processing plasma formed in process space 12 can be formed using a plasma source configured to create a plasma from a process gas. The plasma source can include a parallel-plate, capacitively coupled plasma (CCP) source, an inductively coupled plasma (ICP) source, any combination thereof, and with and without DC magnet systems. Alternatively, the plasma source can include an electrostatic RF (ESRF) source or a microwave device. In another embodiment, the processing plasma in process space 12 can be formed using electron cyclotron resonance (ECR). In yet another embodiment, the processing plasma in process space 12 is formed from the launching of a Helicon wave. In yet another embodiment, the processing plasma in process space 12 is formed from a propagating surface wave.

The plasma processing system 1 can further include a mass sensor 80. The mass sensor 80 can include, for example, a mass spectrometer system to measure gaseous species, such as etch reagents, etch by-products, background gas, and a sensor gas in the processing environment. The mass sensor 80 shown in FIG. 1, is attached to the plasma processing chamber 10. In an alternate embodiment, the mass sensor 80 is located downstream from plasma processing chamber 10.

A controller 26 includes a microprocessor, a memory, and a digital I/O port capable of generating control voltages sufficient to communicate and activate inputs to the processing system 1 as well as monitor outputs from the processing system 1. Moreover, the controller 26 is coupled to and can exchange information with the plasma processing chamber 10, the gas injection system 40, optical diagnostic sensor 22, mass sensor 80, and the vacuum pump system 38. For example, a program stored in the memory can be utilized to control the aforementioned components of a plasma processing system 1 according to a stored process recipe. One example of controller 26 is a DELL PRECISION WORKSTATION 610™, available from Dell Corporation, Dallas, Tex.

Various system components can contain gas emitters that release and expose a sensor gas to a plasma capable of producing characteristic fluorescent light emission to indicate component status in the presence of a plasma. The system components can include, but are not limited to, focus ring 60 containing gas emitter 28, shield 14 containing gas emitter 32, and electrode plate 24 containing gas emitter 34. These exemplary system components are consumable parts that commonly erode during plasma processing, and therefore require status monitoring to facilitate proper replacing.

The role of focus ring 60 that encircles the substrate 35, includes control of the substrate etch rate, etch selectivity, and etch uniformity on the periphery of the substrate 35. The extent of plasma erosion of focus ring 60 is commonly determined ex-situ by removing the focus ring 60 from the plasma processing system 1 and measuring the reduction in the thickness of the focus ring 60. For example, erosion of the order of few tenths of a mm in the thickness of the focus ring 60, can require replacement of the eroded focus ring 60.

During manufacturing of various system components, gas emitters may be integrated into the system component structures to allow monitoring of component status. The integration of gas emitters into system components can be designed so that the gas emitters release a sensor gas that becomes exposed to the plasma environment when the system components need to be replaced. The preferred location (depth) of the gas emitters in the system components can be determined from process history and process requirements.

Various consumable or replaceable components of a plasma processing system are, for example, fabricated from silicon, quartz, alumina, carbon, or silicon carbide. Examples of consumable system components that are fabricated from these materials include electrodes, shields, rings, baffles, and liners. The consumable nature of the replaceable components can require frequent maintenance of the plasma processing system. In addition to the above-mentioned materials, system components (e.g., deposition shields) can be fabricated from metals (e.g., aluminum) and metal alloys (e.g., stainless steel) and require frequent cleaning or replacing.

Monitoring system component status using a mass sensor can include determining if the intensity level of a mass signal associated with a sensor gas released from a system component exceeds a threshold value, arriving at a determination of whether the system component needs to be replaced, and based on the determination, either continuing with the process or stopping the process.

Monitoring system component status using an optical monitoring system can include determining if the intensity level of the fluorescent emission associated with a sensor gas released from a system component exceeds a threshold value, arriving at a determination of whether the system component needs to be replaced, and based on the determination, either continuing with the process or stopping the process.

When the sensor gas released from the gas emitters is excited by a plasma, plasma light is absorbed and subsequently re-emitted as fluorescent light, that is shifted to longer wavelengths than the absorbed plasma light. The absorbed plasma light can, for example, be in the UV region and the emitted fluorescent light can be in the visible region. The shift to longer wavelengths can be advantageous, since light in the visible region is less affected by contaminants, such as polymers and by-products, that can deposit on the optical window 17 of the optical monitoring system 21 during processing. Exposure of the sensor gas released from the gas emitters to energetic species, other than light, in the plasma (e.g., excited gas species), can also result in fluorescent light emission.

The sensor gas can be selected from a wide variety of commercially available gases. The sensor gas can, for example, comprise an inert gas. The inert gas can, for example, comprise at least one of He, Ne, Ar, Kr, Xe. In addition, the sensor gas can comprise at least one of $N_2$, $O_2$, NO, and $N_2O$. The sensor gas can contain at least one gas having fluorescent properties corresponding to a light wavelength produced in a plasma. The sensor gas can be selected in view of the desired fluorescent properties, that can depend on the plasma species, and the plasma chemistry. Furthermore, the sensor gas can be selected in view of ease of detection by a mass sensor. In order to increase the detection sensitivity, a sensor gas can be selected that is different from other gases present in the plasma processing chamber. The selection of a sensor gas may be evaluated in view of possible contamination of the process environment, due to exposure of the sensor gas to the plasma. The above-identified sensor gases are exemplary; a wide variety of other sensor gases can be utilized.

FIG. 2A shows a plan view of a system component containing a plurality of gas emitters. In the exemplary embodiment shown in FIG. 2A, the system component is a ring 61. The ring 61 can, for example, be a focus ring, an insulator ring, or a shield ring. Gas emitters 28a–28d, capable of releasing a sensor gas emitting fluorescent light when exposed to a plasma, are integrated into the ring 61. The number of gas emitters shown in FIG. 2A is exemplary; any number of gas emitters can be utilized. The gas emitters 28a–28d can contain at least one gas capable of fluorescent emission when exposed to a plasma. The gas emitters can contain different gases, or alternatively, the gas emitters can contain the same gas(es). Although the gas emitters 28a–28d are shown as squares in the embodiment in FIG. 2A, this is not required for the invention. In alternate embodiments, the gas emitters can have different shapes including non-geometrical and/or geometrical shapes, such as rectangular, circular, elliptical, and triangular shapes.

The internal volume of a gas emitter containing a sensor gas can be contained in a plug that can be easily inserted into the consumable part. Alternatively, the internal volume can be machined into the consumable part, the volume filled with a sensor gas, and the volume sealed from the exterior environment.

FIG. 2B shows a cross-sectional view of the system component in FIG. 2A. Although the cross-sectional shape of gas emitter 28b is shown as a rectangle in the embodiment in FIG. 2B, this is not required for the invention. In alternate embodiments, the gas emitter's cross-section can have different shapes including non-geometrical and/or geometrical shapes (e.g., as discussed with respect to FIG. 2A). The gas emitter 28b can be fully encapsulated by the ring material (e.g., quartz, alumina, or silicon) such that the cover portion 27b over the gas emitter 28b is made of the same material as the rest of the surrounding material 29b of the ring. Alternatively, the gas emitter 28b can be partially encapsulated within the surrounding material 29b but covered by a cover portion 27b of a different material.

Figure 2D:
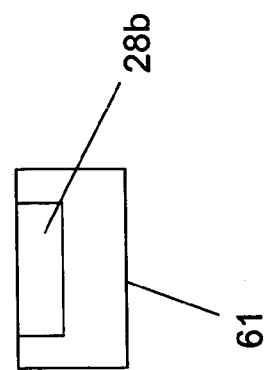
FIG. 2D shows a cross-sectional view of the system component in FIG. 2C.
Figure 2C:
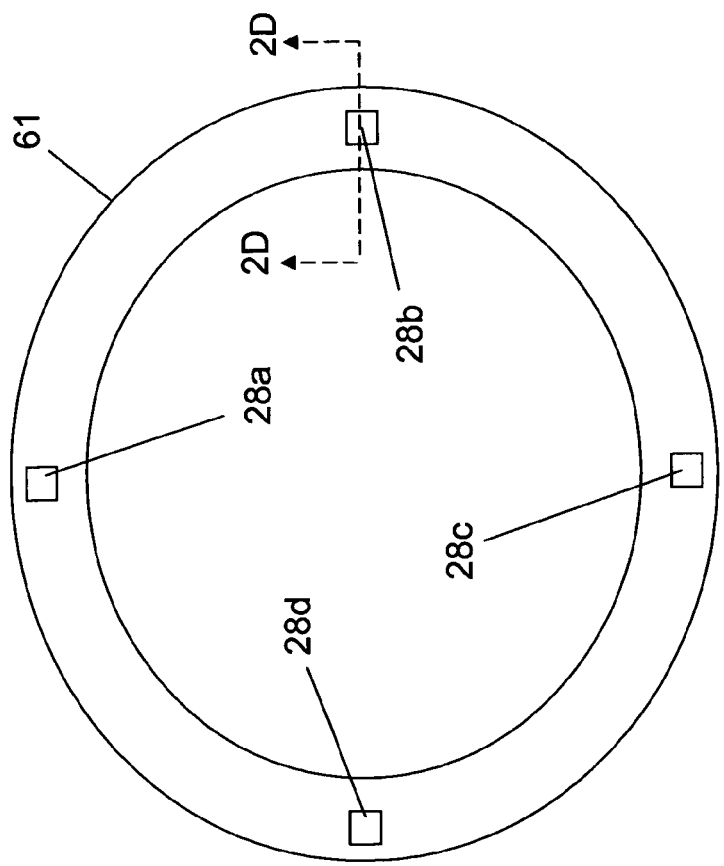
FIG. 2C shows a plan view of an eroded system component containing a plurality of gas emitters.

FIG. 2C shows a plan view of an eroded system component containing a plurality of gas emitters. Exposure of the ring 61 in FIG. 2A to a plasma, can result in erosion of the ring 61 and release of one or more of the gases from gas emitters 28a–28d to the plasma. Optical monitoring of the process space 12, and the onset of or significant increase in characteristic fluorescent light emission from at least one sensor gas, can be utilized to determine whether the system component needs to be replaced. Furthermore, the onset of or significant increase in a mass signal corresponding to at least one sensor gas, can be utilized to determine whether the system component needs to be replaced. FIG. 2D shows a cross-sectional view of the system component in FIG. 2C. In FIG. 2D the sensor gas has been released by the gas emitter 28b into the process environment.

FIG. 3A shows a plan view of a system component containing a plurality of gas emitters. In the embodiment shown in FIG. 3A, the system component is a ring 61. Emitters 28a–28d, can be integrated into a surface of the ring 61 that is exposed to the process space 12. FIG. 3B shows a cross-sectional view of the system component in FIG. 3A. The gas emitter 28b in FIG. 3B is connected to a gas supply line 100 to provide a gas to the emitter 28b. The pressure of the sensor gas in the volume of the gas emitter 28b and the flow of a sensor gas into the gas emitter 28 can be constantly controlled and monitored by a pressure controller (not shown). The gas supply line 100 can be coupled to a gas source such as a high pressure gas cylinder (not shown). The gas supply line 100 can be sealed between the system component 61 and the respective mating component using, but not limited to, a sealing device such as an O-ring. As would be understood by one of ordinary skill in the art, various techniques may be used to supply the sensor gas to the gas emitter.

Figure 3D:
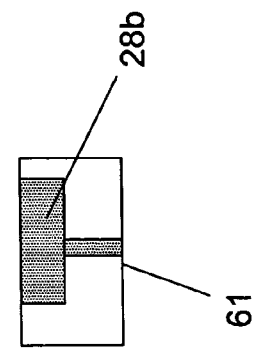
FIG. 3D shows a cross-sectional view of the system component in FIG. 3C.
Figure 3C:
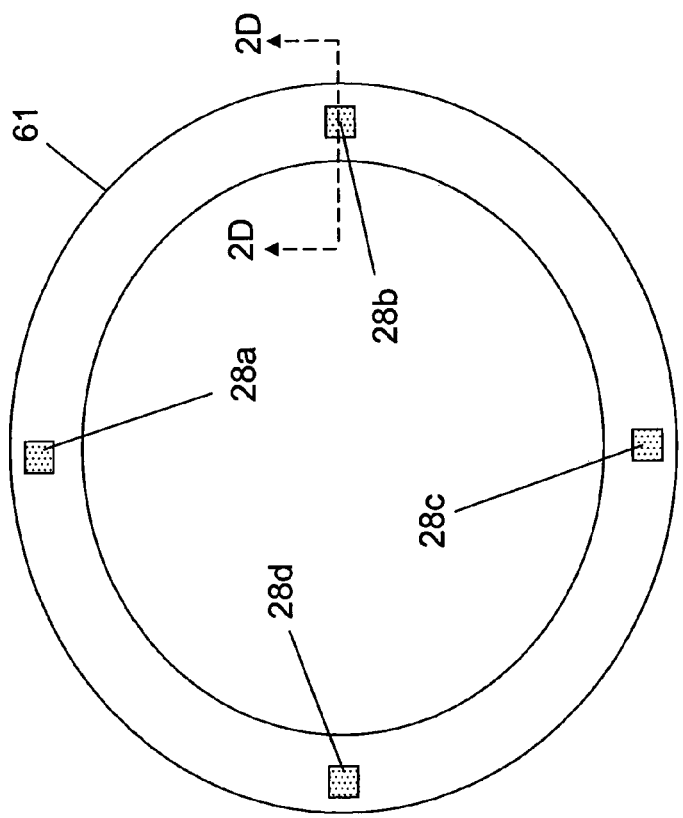
FIG. 3C shows a plan view of an eroded system component containing a plurality of gas emitters.

FIG. 3C shows a plan view of an eroded system component. Exposure of the ring 61 in FIG. 3A to a plasma, can result in erosion of the ring 61 and release of a sensor gas from one or more of the gas emitters 28a–28d. Optical monitoring of the plasma processing system, and the appearance of or significant increase in the characteristic fluorescent light emission from the release of a sensor gas from the ring 61 can be utilized to determine whether the system component needs to be replaced. Furthermore, the onset of or significant increase in a mass signal corresponding to at least one sensor gas, can be utilized to determine whether the system component needs to be replaced. FIG. 3D shows a cross-sectional view of the system component in FIG. 3C. In FIG. 3D the sensor gas is being released by the gas emitter 28b into the process environment.

Figure 4A:
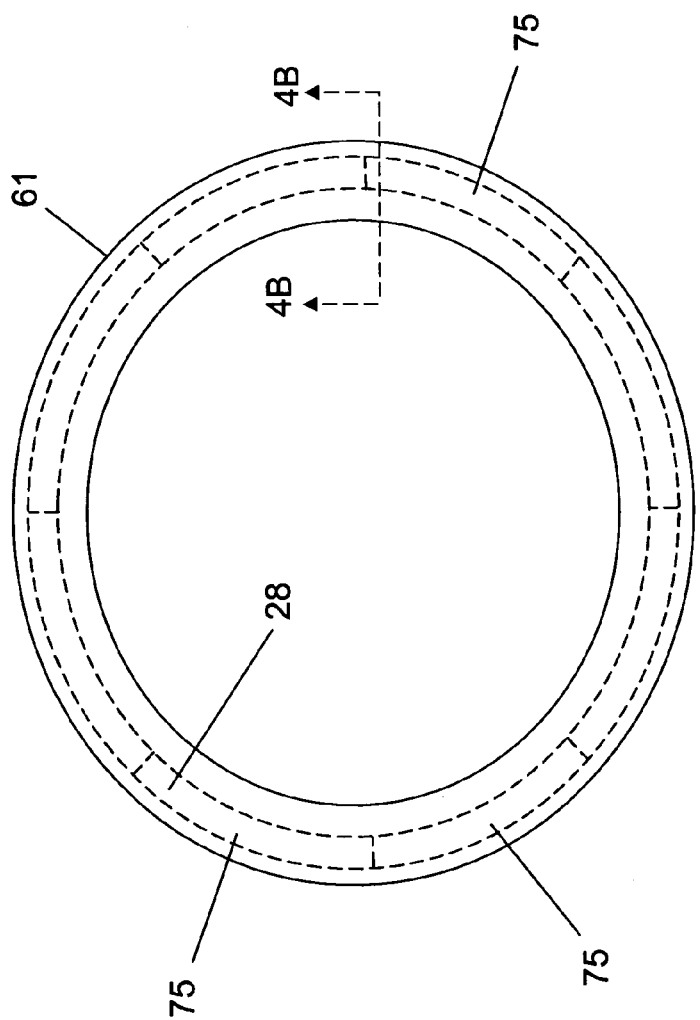
FIG. 4A shows a plan view of a system component containing a gas emitter.
Figure 4B:
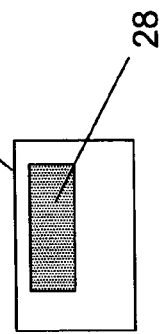
FIG. 4B shows a cross-sectional view of the system component in FIG. 4A.

FIG. 4A shows a plan view of a system component containing a gas emitter. In the embodiment shown in FIG. 4A, the system component is a ring 61 (having various subsections 75) that encircles substrate 35. The gas emitter 28 is ring shaped and fully encapsulated by the ring material. Alternatively, the emitter can be partially encapsulated by the ring material. FIG. 4B shows a cross-sectional view of the system component in FIG. 4A. Each subsection 75 may contain one or more sensor gases. Moreover, the one or more sensor gases may change from subsection-to-subsection, or may be constant across all subsections 75. Although depicted as containing 8 subsections 75, the number of subsections may be varied to provide varying amounts of spatial resolution of the erosion of the ring 61.

Figure 5B:
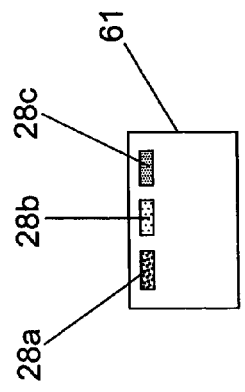
FIG. 5B shows a cross-sectional view of the system component in FIG. 5A.
Figure 5A:
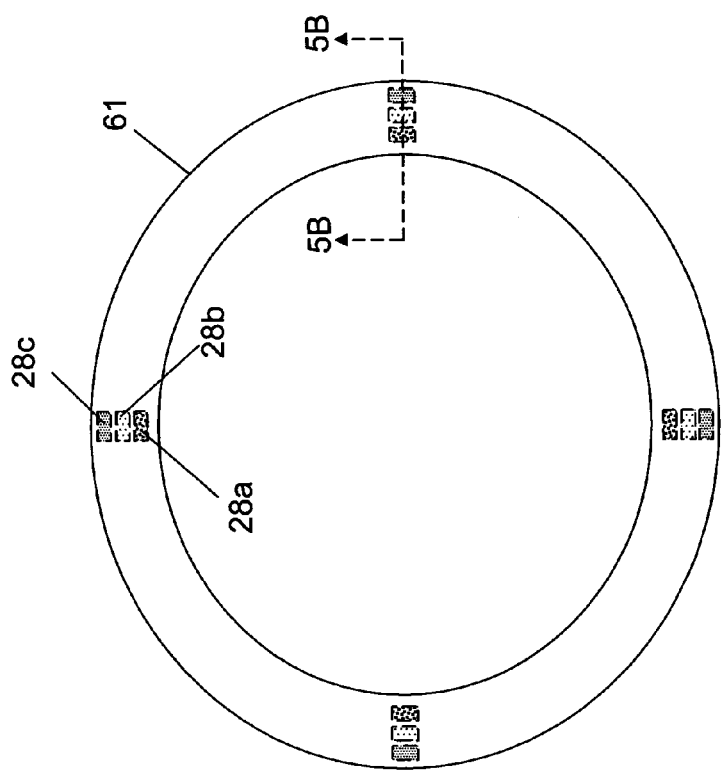
FIG. 5A shows a plan view of a system component containing a plurality of gas emitters.

FIG. 5A shows a plan view of a system component containing a plurality of gas emitters. In the embodiment shown in FIG. 5A, the system component is a ring 61. Gas emitters 28a–28c, capable of releasing a sensor gas emitting fluorescent light when exposed to a plasma, are integrated into the ring 61 at different radial positions and are fully encapsulated by the ring material. Alternatively, the gas emitters 28a–28c can be integrated into the ring 61 at the same radial positions. The number of gas emitters shown in FIG. 5A is exemplary; any number of gas emitters can be utilized. The gas emitters 28a–28c can contain at least one sensor gas. The gas emitters can contain different sensor gases, or alternatively, the gas emitters can contain the same sensor gases. By using one set of sensor gases at one location (e.g., at zero degrees on the unit circle) and by using a different set of sensor gases at other locations (e.g., at 90, 180 and 270 degrees on the unit circle), the optical emissions of the ring 61 can be spatially resolved. FIG. 5B shows a cross-sectional view of the system component in FIG. 5A.

Figure 5C:
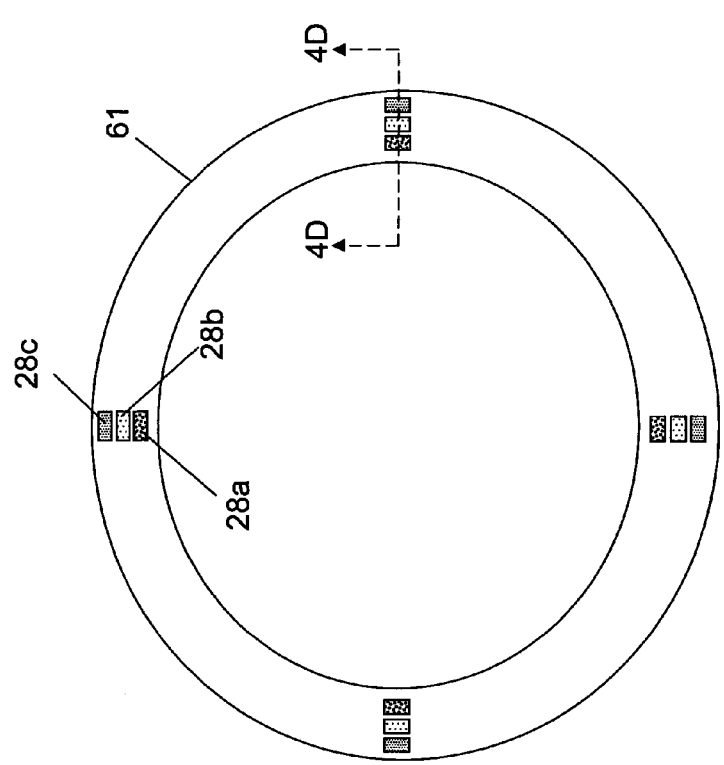
FIG. 5C shows a plan view of an eroded system component.

FIG. 5C shows a plan view of an eroded system component. Exposure of the ring 61 in FIG. 5C to a plasma, can result in erosion of the ring 61 and release of a sensor gas from one or more of the gas emitters 28a–28c to the plasma. Optical monitoring of the plasma processing system, and the onset of or significant increase in characteristic fluorescent light emission can be utilized to determine whether the system component needs to be replaced. Furthermore, the onset of or significant increase in a mass signal corresponding to at least one sensor gas, can be utilized to determine whether the system component needs to be replaced.

Figure 5D:
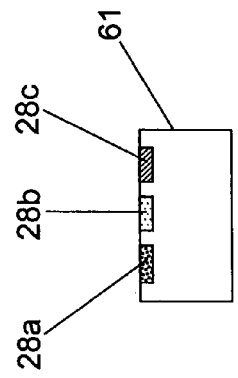
FIG. 5D shows a cross-sectional view of the system component in FIG. 5C.

FIG. 5D shows a cross-sectional view of the system component in FIG. 5C. If the ring 61 erodes uniformly, fluorescent light emission from gases released from gas emitters 28a–28c can appear substantially at the same time. However, if the ring 61 etches non-uniformly (not shown) during plasma processing, the characteristic fluorescent light emission and a mass signal from one or more sensor gases released from gas emitters 28a–28c can provide spatial erosion information, in addition to the extent of the erosion.

FIG. 6A shows a plan view of a system component containing a plurality of gas emitters. In the embodiment shown in FIG. 6A, the system component is a ring 61. Gas emitters 28a–28c, capable of releasing a sensor gas emitting fluorescent light when exposed to a plasma, are integrated into the ring 61 as concentric rings at different radial positions and are fully encapsulated by the ring material. The number of emitters shown in FIG. 6A is exemplary; any number of emitters can be utilized. The gas emitters 28a–28c can contain at least one sensor gas. The emitters can contain different sensor gases, or alternatively, the emitters can contain the same sensor gases. FIG. 6B shows a cross-sectional view of the system component in FIG. 6A. Spatial distribution of emitters 28a, 28b, and 28c can be used to measure non-uniform erosion of the system component.

Figure 7A:
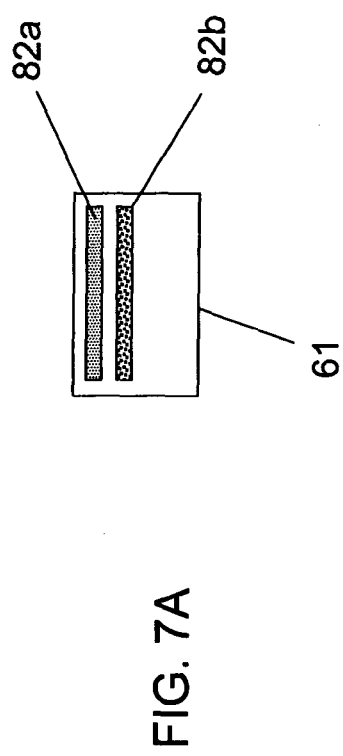
FIG. 7A shows a cross-sectional view of a system component containing a plurality of gas emitters.

FIG. 7A shows a cross-sectional view of a system component containing a gas emitter stack including gas emitters 82a and 82b. In the embodiment shown in FIG. 7A, the system component is a ring 61. In a first embodiment of the stack, shown in FIGS. 7A–7D, the gas emitters 82a and 82b each contain a different type of a sensor gas such that following the erosion of gas emitter 82a, the erosion of emitter 82b is signaled by a change to a new emission type. In a second embodiment, the emitters 82a and 82b contain the same type of a sensor gas such that following the erosion of gas emitter 82, the erosion of emitter 82b is signaled by the same emission type but is delayed.

Figure 7B:
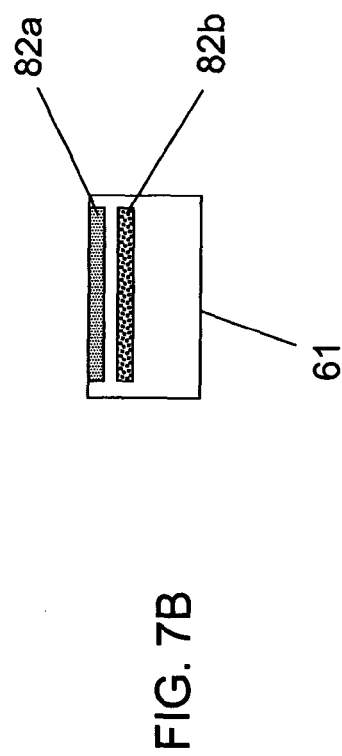
FIG. 7B shows a cross-sectional view of an eroded system component containing a plurality of gas emitters.

FIG. 7B shows a cross-sectional view of an eroded system component containing an emitter stack. Exposure of the ring 61 in FIG. 7A to a plasma, can result in erosion of the ring 61 and release and exposure of a sensor gas from gas emitter 82a to the plasma. In a first embodiment, optical monitoring of the plasma processing system, and the onset of or significant increase in characteristic fluorescent light emission due to sensor gas being released from the gas emitter 82a, can be utilized to determine the status of the ring. In addition, disappearance of a characteristic fluorescent light emission from an emitter can be used to determine the status of the ring.

Figure 7D:
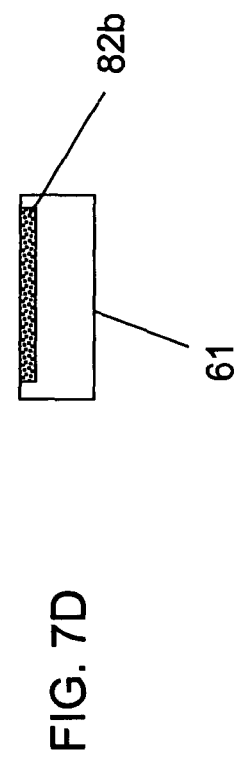
FIG. 7D shows a cross-sectional view of an eroded system component containing a plurality of gas emitters.
Figure 7C:
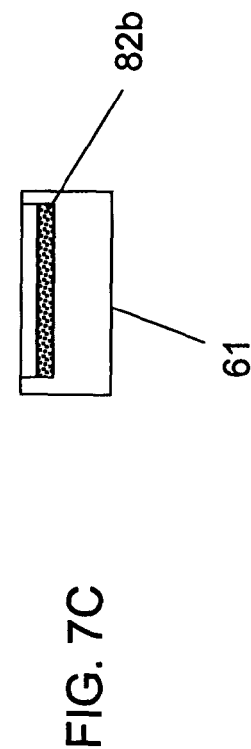
FIG. 7C shows a cross-sectional view of an eroded system component containing a plurality of gas emitters.

FIG. 7C shows a cross-sectional view of an eroded system component containing an emitter stack. Further exposure of the ring 61 in FIG. 7C to a plasma, can result in removal of the system component material separating the gas emitters 82a and 82b.

FIG. 7D shows a cross-sectional view of an eroded system component containing an emitter stack. Further exposure of the ring 61 in FIG. 7C to a plasma, can result in release and exposure of a sensor gas from emitter 82b to the plasma. Optical monitoring of the plasma processing system, and the onset of or significant increase in characteristic fluorescent light emission from a sensor gas released from emitter 82b can be utilized to determine the status of the ring. Furthermore, the onset of or significant increase in a mass signal corresponding to a sensor gas, can be utilized to determine the status of the ring.

Figure 8B:
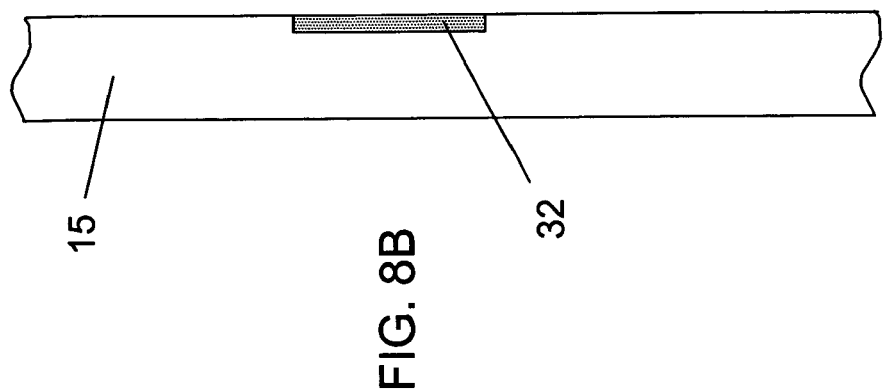
FIG. 8B shows a cross-sectional view of an eroded system component containing a gas emitter.
Figure 8A:
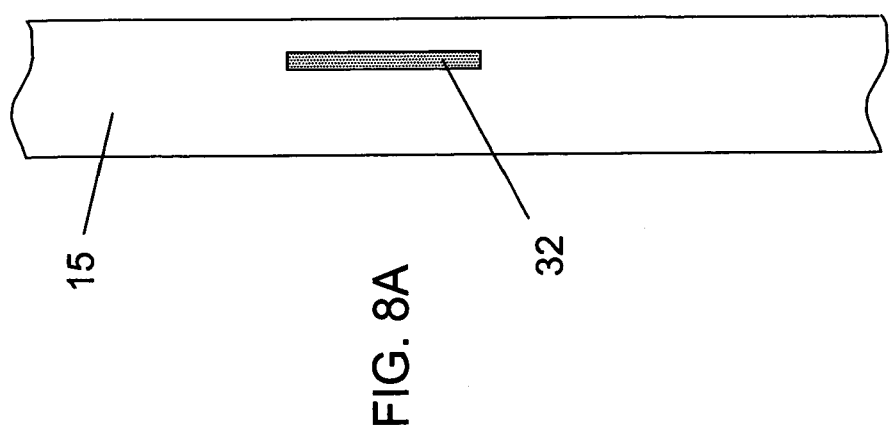
FIG. 8A shows a cross-sectional view of a system component containing a gas emitter.

FIG. 8A shows a cross-sectional view of a system component containing a gas emitter. In the embodiment shown in FIG. 8A, the system component 15 can, for example, be a ring, a shield, an electrode, a baffle, or a liner. In one embodiment the system component 15 is shield that reduces erosion of chamber walls during plasma processing. A gas emitter 32, containing at least one sensor gas capable of emitting fluorescent light when exposed to a plasma, is integrated into the system component 15. The emitter 32 is fully encapsulated by the ring material (e.g., quartz or alumina).

FIG. 8B shows a cross-sectional view of an eroded system component containing a gas emitter. During plasma processing, the system component 15 can be exposed to the plasma environment and this can result in erosion of the system component 15, and release and exposure of a sensor gas from gas emitter 32 to the plasma environment. Optical monitoring of the plasma processing system, and the onset of or significant increase in characteristic fluorescent light emission from the gas released from emitter 32, can be utilized to determine whether the system component needs to be replaced. Furthermore, the onset of or significant increase in a mass signal corresponding to a sensor gas, can be utilized to determine whether the system component needs to be replaced.

Figure 9C:
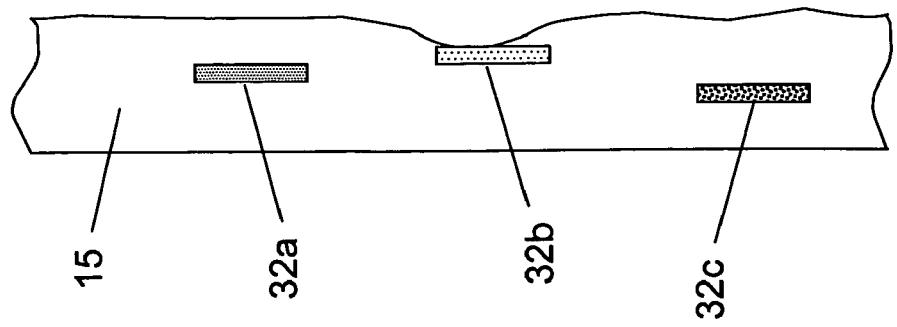
FIG. 9C shows a cross-sectional view of an eroded system component containing a plurality of gas emitters.
Figure 9B:
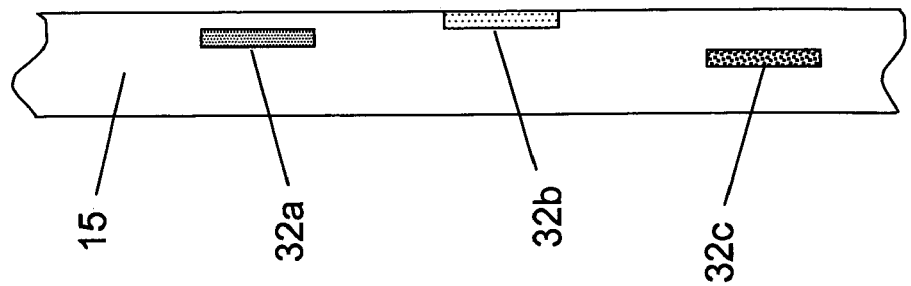
FIG. 9B shows a cross-sectional view of an eroded system component containing a plurality of gas emitters.
Figure 9A:
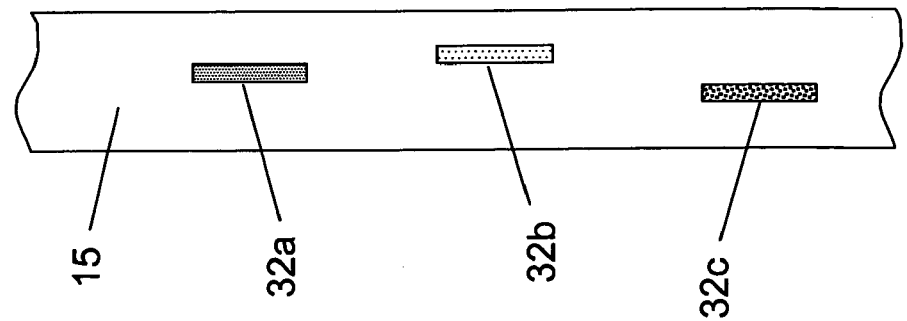
FIG. 9A shows a cross-sectional view of a system component containing a plurality of gas emitters.

FIG. 9A shows a cross-sectional view of a system component containing a plurality of gas emitters. In the embodiment shown in FIG. 9A, the system component 15 contains gas emitters 32a–32c that are fully encapsulated by the system component material. While illustrated as being embedded at different depths, alternatively, the gas emitters 32a–32c could be embedded at the same depth. As would be appreciated, the depth of each emitter to be buried within the surface may be determined empirically by examining eroded surfaces and when such erosion decreased system performance or cleanliness.

FIG. 9B shows a cross-sectional view of an eroded system component containing a plurality of gas emitters. The system component 15 is uniformly eroded, and fluorescent signals from sensor gases released from gas emitters 32a–32c can appear substantially at the same time. FIG. 9C shows a cross-sectional view of an eroded system component containing a plurality of gas emitters. If the system component 15 etches non-uniformly during plasma processing, the characteristic fluorescent light emission from gases released from one or more of gas emitters 32a–32c can provide spatial erosion information, in addition to information on the extent of the erosion.

In alternate embodiments, gas emitters can be integrated into system components by depositing a protective barrier on the surfaces of system components containing at least one gas emitter. The role of a protective barrier can be to reduce erosion of the system components during plasma processing. A protective barrier can be substantially transparent to plasma light over a wide range of wavelengths. A protective barrier comprising, for example Yttria ($Y_2O_3$), can be formed using (thermal) spray coating techniques that are well known to those skilled in the art of ceramic spray coatings. In an alternate embodiment, forming the protective barrier can further comprise polishing the thermal spray coating. For example, polishing the thermal spray coating can comprise the application of sand paper to the sprayed surfaces. The protective barrier can comprise at least one of $Y_2O_3$, $Sc_2O_3$, $Sc_2F_3$, $YF_3$, $La_2O_3$, $CeO_2$, $Eu_2O_3$, $DyO_3$, $SiO_2$, $MgO$, $Al_2O_3$, $ZnO$, $SnO_2$, and $In_2O_3$. The protective barrier thickness can range from 0.5 microns to 500 microns, for example. Alternatively, the protective barrier can comprise a phosphor material, e.g. $Y_2O_3$:Eu. Disappearance of a characteristic fluorescent light emission from a phosphor material in a protective barrier coupled with a release of a sensor gas from gas emitter can be used to determine the status of a system component.

Figure 10:
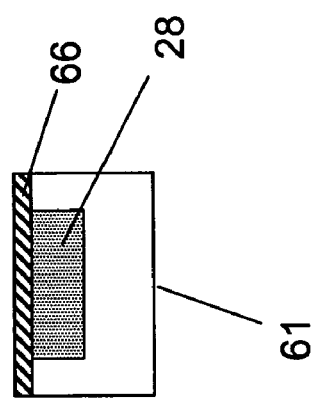
FIG. 10 shows a cross-sectional view of a system component containing a gas emitter and a protective layer.

FIG. 10 shows a cross-sectional view of a system component containing a gas emitter. In FIG. 10, the system component is a ring 61. The ring 61 can, for example, be a focus ring, an insulator ring, or a shield ring. A protective barrier layer 66 is deposited on the gas emitter 28 and system component 61 to reduce erosion. A mass signal and fluorescent emissions corresponding to a sensor gas released from gas emitter 28 during plasma processing can indicate erosion of the protective barrier layer 66.

Figure 11:
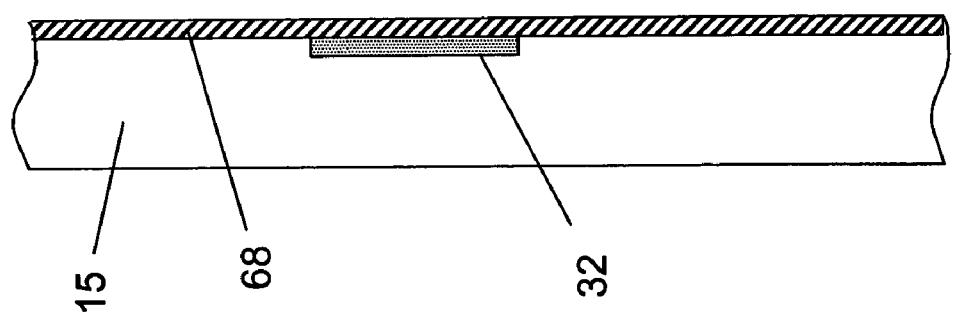
FIG. 11 shows a cross-sectional view of a system component containing a gas emitter and a protective layer.

FIG. 11 shows a cross-sectional view of a system component containing an gas emitter. In the embodiment shown in FIG. 11, the system component 15 can, for example, be a ring, a shield, an electrode, a baffle, or a liner. A protective barrier layer 68 is deposited on the gas emitter 32 and system component 15 to reduce erosion. A mass signal and fluorescent emissions corresponding to a sensor gas released from gas emitter 32 during plasma processing can indicate erosion of the protective barrier layer 68.

The status of a system component can be determined during plasma processing, by monitoring the characteristic fluorescent emission from as sensor gas released from a gas emitter integrated into the system component. One possible method for determining the status of a system component is to use optical emission spectroscopy (OES) to monitor a wavelength range where the characteristic fluorescent emission occurs. Another possible method for determining the status of a system component is to use a mass sensor to monitor a mass signal from a sensor gas. A system component can contain at least one gas emitter, that is capable of releasing a sensor gas with fluorescent emission at characteristic wavelength(s) when exposed to a plasma, that allows for identification of the system component. Furthermore, the sensor gas can be identified using a mass sensor. When an intensity level of an emission with a characteristic wavelength and an intensity level of a mass signal corresponding to a sensor gas, crosses a specified threshold value (e.g., increase above a particular value), a determination can be made whether the system component needs to be replaced, and based on the determination, the process can be continued or stopped.

Figure 12:
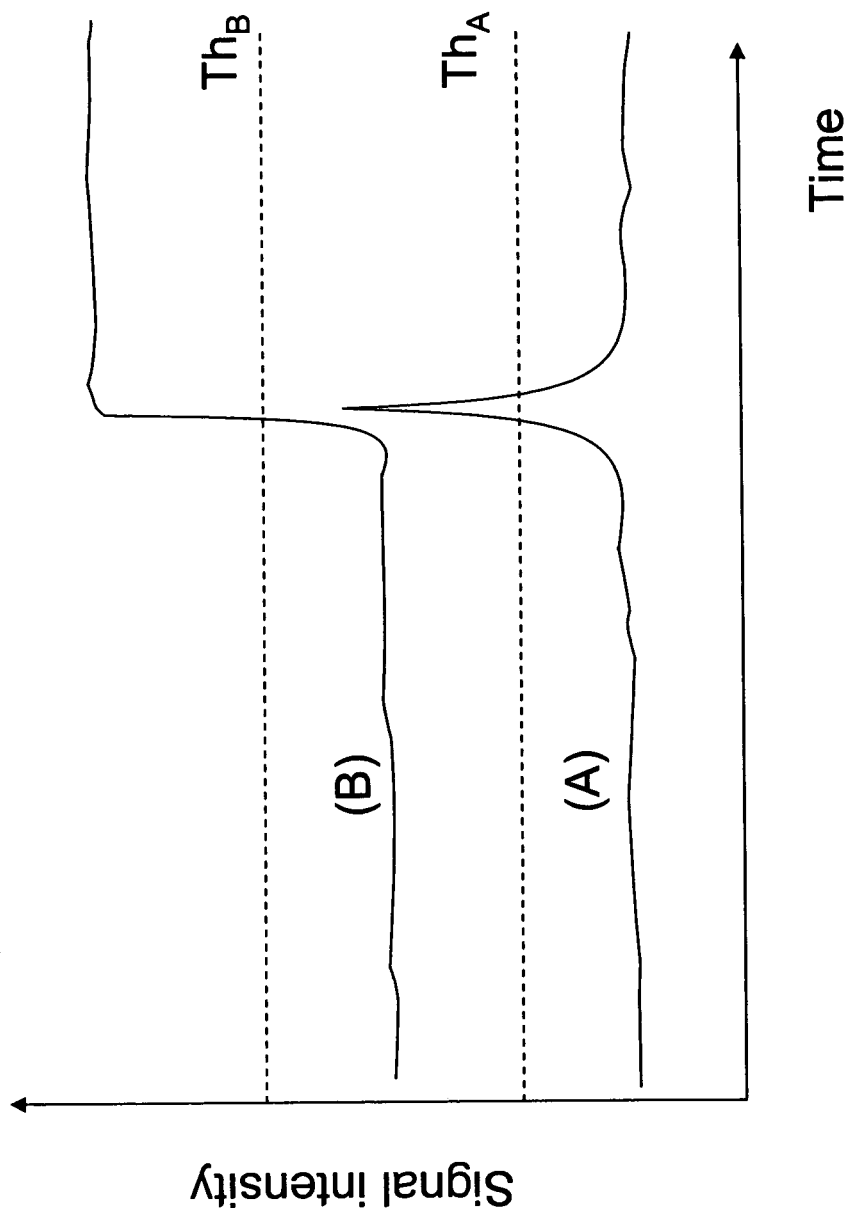
FIG. 12 schematically shows signal intensity of a sensor gas released from a gas emitter.

FIG. 12 schematically shows signal intensity of a sensor gas released from a gas emitter. The signal intensity is plotted as a function of processing time. Curve (A) shows signal intensity of a sensor gas released from a gas emitter containing a fixed amount of sensor gas in a closed volume (e.g., see FIG. 2). Curve (B), which has been offset from curve (A) for clarity, shows signal intensity of a sensor gas released from a gas emitter that is connected to a gas supply line (e.g., see FIG. 3). When the intensity levels in curves (A) and (B) cross threshold intensity levels $Th_A$ and $Th_B$, a determination can be made whether the system component needs to be replaced, and based on the determination, the process can be continued or stopped.

Figure 13:
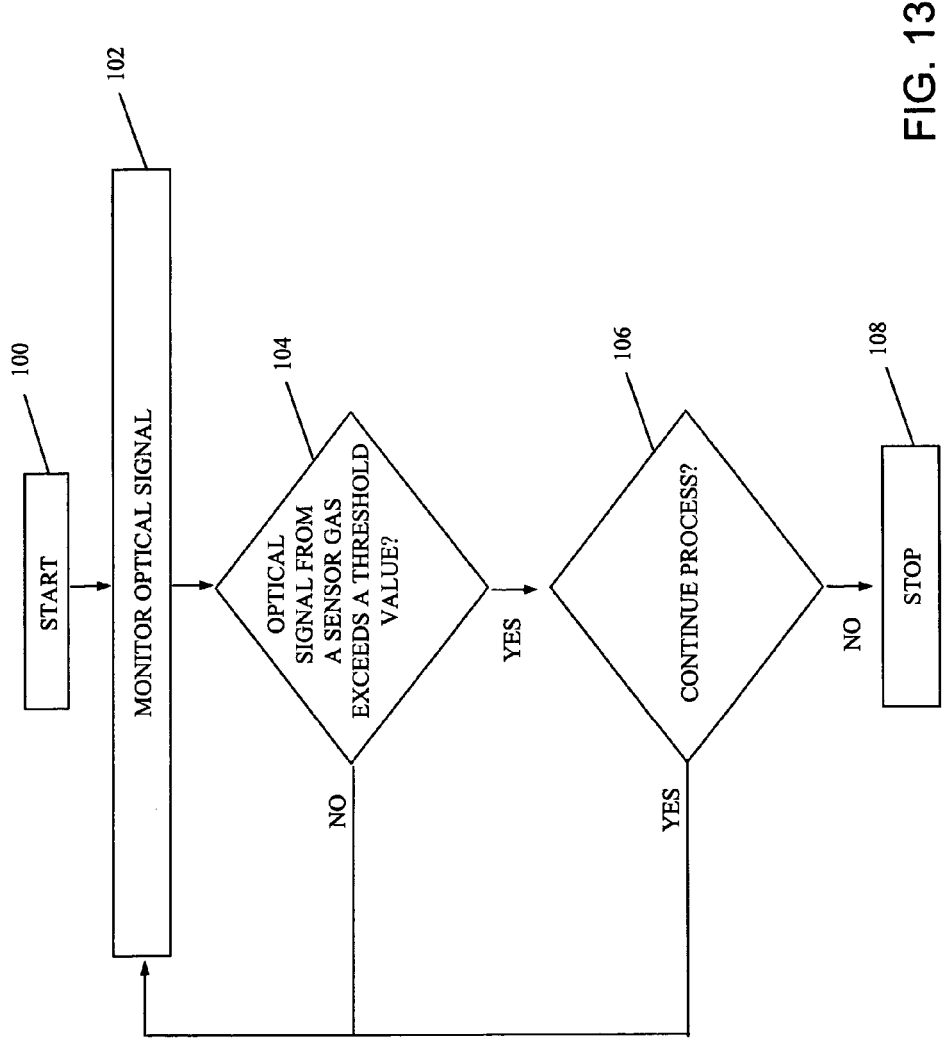
FIG. 13 is a flowchart for monitoring the status of system components using optical emission.

FIG. 13 is a flowchart for monitoring the status of system components using optical emission. In step 100, the process is started. In step 102, an optical signal from the plasma processing region is monitored using an optical monitoring system. In step 104, the optical signal is analyzed for characteristic light emission from a sensor gas released from a gas emitter integrated into a system component. If the characteristic light emission from the gas exceeds a threshold value, a determination is made in step 106 on whether to continue the process or to stop the process in step 108.

Determining whether the process should be continued in step 106 can depend on the fluorescent emission that is detected, e.g., identifying the system component. Furthermore, fluorescent emission from sensor gases released from a plurality of gas emitters integrated into a system component can indicate if the system component is eroding uniformly during plasma processing and can therefore provide spatial erosion information, in addition to the extent of the erosion.

FIG. 14 is a flowchart for monitoring the status of system components using a mass sensor. In step 100, the process is started. In step 102, a mass signal from the processing region is monitored using a mass sensor. In step 104, the mass signal is monitored and analyzed for a sensor gas released from an emitter integrated into a system component. If the amount of a sensor gas species exceeds a threshold value, a determination is made in step 106 on whether to continue the process or to stop the process in step 108.

Determining whether the process should be continued in step 106 can depend on the sensor gas that is detected, e.g., identifying the system component. Furthermore, mass signals from sensor gases released from a plurality of emitters integrated into a system component can indicate if the system component is eroding uniformly during plasma processing and can therefore provide spatial erosion information, in addition to the extent of the erosion.

This method of monitoring the status of system components using gas emitters, provides a new in-situ method for monitoring erosion of system components in a plasma environment. The consumption of consumable system components can be monitored during plasma processing, without the need for disassembly of the plasma processing system. The method can significantly reduce the risk of overdue or premature replacement of consumable components, and avoid processing conditions that are outside process specifications due to erosion of system components.

It should be understood that various modifications and variations of the present invention may be employed in practicing the invention. It is therefore to be understood that, within the scope of the appended claims, the invention may be practiced otherwise than as specifically described herein.

The invention claimed is:

1. A method of monitoring erosion of a system component in a plasma processing system, the method comprising:
    exposing a system component having a gas emitter to a plasma process, wherein the gas emitter comprises a discrete cavity having a predetermined shape and is embedded within the system component to contain a sensor gas therein; and
    monitoring the plasma processing system for release of a sensor gas from the gas emitter during said process to determine erosion of the system component.

2. The method according to claim 1, wherein said exposing comprises exposing a consumable part to said process.

3. The method according to claim 1, wherein said exposing comprises exposing at least one of a ring, a shield, an electrode, a baffle, and a liner to said process.

4. The method according to claim 1, wherein said monitoring comprises monitoring at least one gas having fluorescent properties when excited by a light produced in the plasma.

5. The method according to claim 1, wherein said monitoring comprises monitoring at least one gas having fluorescent properties when excited by excited gas species produced in the plasma.

6. The method according to claim 1, wherein said monitoring comprises using an optical monitoring system to detect fluorescent light emission.

7. The method according to claim 6, wherein said monitoring further comprises determining if the intensity level of the fluorescent emission exceeds a threshold value.

8. The method according to claim 7, wherein said monitoring further comprises identifying the system component from a detected wavelength of the fluorescent light emission.

9. The method according to claim 7, wherein said monitoring further comprises measuring an intensity level of the fluorescent emission to arrive at a determination of whether the component needs to be replaced, and based on the determination, either continuing with the process or stopping the process.

10. The method according to claim 1 wherein said monitoring comprises using a mass sensor to detect a mass signal.

11. The method according to claim 10, wherein said monitoring further comprises determining if an intensity level of the mass signal exceeds a threshold value.

12. The method according to claim 10, wherein said monitoring further comprises identifying the system component from the mass signal.

13. The method according to claim 10, wherein said monitoring further comprises measuring an intensity level of a mass signal to arrive at a determination of whether the component needs to be replaced, and based on the determination, either continuing with the process or stopping the process.

14. The method according to claim 1, wherein said monitoring comprises monitoring for release of at least one of He, Ne, Ar, Kr, Xe, $N_2$, $O_2$, NO, and $N_2O$.

15. The method according to claim 1, wherein said monitoring comprises monitoring for release of a fixed amount of said sensor gas contained in an enclosed volume of said gas emitter.

16. A plasma processing system, comprising:
a plasma processing chamber;
a plasma source configured to create a plasma from a process gas;
a system component having a gas emitter, wherein the gas emitter comprises a discrete cavity having a predetermined shape and is embedded within the system component to contain a sensor gas therein;
a monitoring system configured to monitor for the release of the sensor gas from the gas emitter to determine erosion level of the system component; and
a controller configured to control the plasma processing system.

17. The system according to claim 16, wherein the system component comprises a consumable part.

18. The system according to claim 16, wherein the sensor gas comprises at least one gas having fluorescent properties when excited by a light produced in the plasma.

19. The system according to claim 16, wherein the sensor gas comprises at least one gas having fluorescent properties when excited by excited gas species produced in the plasma.

20. The system according to claim 16, wherein the monitoring system comprises an optical monitoring system for monitoring fluorescent light emission from the plasma processing chamber during processing.

21. The system according to claim 16, wherein the monitoring system comprises a mass sensor for monitoring a mass signal from the plasma processing chamber during processing.

22. The system according to claim 16, wherein the system component comprises at least one of a ring, a shield, an electrode, a baffle, and a liner.

23. The system according to claim 16 wherein the system component comprises at least one of silicon, quartz, alumina, carbon, silicon carbide, aluminum, and stainless steel.

24. The system according to claim 16, wherein the system component further comprises a protective barrier.

25. The system according to claim 24, wherein the protective barrier comprises at least one of $Y_2O_3$, $Sc_2O_3$, $Sc_2F_3$, $YF_3$, $La_2O_3$, $CeO_2$, $Eu_2O_3$, $DyO_3$, $SiO_2$, MgO, $Al_2O_3$, ZnO, $SnO_2$, and $In_2O_3$.

26. The system according to claim 16, wherein the plasma source comprises an inductive coil.

27. The system according to claim 16, wherein the plasma source comprises a plate electrode.

28. The system according to claim 16, wherein the plasma source comprises at least one of an ECR source, an ESPY source, a microwave device, a Helicon wave source, and a surface wave source.

29. The plasma processing system of claim 16,
wherein the gas emitter contains a sensor gas capable of fluorescent light emission when exposed to a plasma;
an optical monitoring system for monitoring light emission from the plasma processing chamber during processing to monitor erosion level of the system component, wherein the optical monitoring system is further configured to identify the system component from a wavelength of the fluorescent light emission, to determine if an intensity level of the fluorescent emission exceeds a threshold value, to determine if the system component needs to be replaced, and based on the determination, either continue with the process or stop the processad.

30. The plasma processing system of claim 16, further comprising:
a mass sensor for monitoring a mass signal from the plasma processing chamber during processing to monitor erosion level of the system component; wherein the mass sensor is further configured to identify the system component from the mass signal, to determine if an intensity level of the mass signal exceeds a threshold value, to determine if the system component needs to be replaced, and based on the determination, either continue with the process or stop the process.

31. The system according to claim 17, wherein said gas emitter comprises a closed volume that is fully encapsulated within said system component to contain a fixed amount of sensor gas within the gas emitter.

32. A monitorable consumable system component, comprising:
a system element that is consumed during processing performed by the system; and
a gas emitter being a discrete cavity having a predetermined shape and embedded within the system element to contain a sensor gas therein.

33. The consumable system component according to claim 32, wherein the sensor gas is capable of fluorescent light emission when exposed to a plasma.

34. The consumable system component according to claim 33, wherein the light emission is used to monitor erosion level of the system component.

35. The consumable system component according to claim 32, wherein a mass signal is used to monitor erosion level of the system component.

36. The consumable system component according to claim 32, wherein the system element comprises a ring, a shield, an electrode, a baffle, or a liner.

37. The consumable system component according to claim 32, wherein the system element comprises a focus ring.

38. The consumable system component according to claim 32, wherein the system element comprises an electrode plate.

39. The consumable system component according to claim 32, wherein the system element comprises a deposition shield.

40. The consumable system component according to claim 32, wherein the system element comprises at least one of silicon, quartz, alumina, carbon, silicon carbide, aluminum, and stainless steel.

41. The consumable system component according to claim 32, wherein the gas emitter is fully encapsulated by the system element to provide a closed volume that contains a fixed amount of sensor gas within the gas emitter.

42. The consumable system component according to claim 32, wherein a light emission from the sensor gas allows for identifying the consumable system component.

43. The consumable system component according to claim 32, wherein a mass signal from the sensor gas allows for identifying the consumable system component.

44. The consumable system component according to claim 32, wherein the sensor gas comprises at least one of He, Ne, Ar, Kr, Xe, $N_2$, $O_2$, NO, and $N_2O$.

45. The consumable system component according to claim 32, wherein the system component further comprises a protective barrier.

46. The consumable system component according to claim 45, wherein the protective barrier comprises at least one of $Y_2O_3$, $Sc_2O_3$, $Sc_2F_3$, $YF_3$, $La_2O_3$, $CeO_2$, $Eu_2O_3$, $DyO_3$, $SiO_2$, MgO, $Al_2O_3$, ZnO, $SnO_2$, and $In_2O_3$.

47. A monitorable consumable system component, comprising:
a system element that is consumed during processing performed by the system; and
a gas emitter containing a sensor gas coupled to the system element, further comprising a gas supply line configured to connect said gas emitter to a sensor gas source that supplies said sensor gas to the gas emitter.

48. A method of monitoring erosion of a system component in a plasma processing system, the method comprising:
exposing a system component having a gas emitter to a plasma process; and
monitoring the plasma processing system for release of a sensor gas from the gas emitter during said process to determine erosion of the system component, wherein said monitoring comprises monitoring for release of said sensor gas from said gas emitter, a supply of sensor gas being supplied from a gas source to said gas emitter.

49. A plasma processing system, comprising:
a plasma processing chamber;
a plasma source configured to create a plasma from a process gas;
a system component having a gas emitter, wherein the gas emitter contains a sensor gas;
a monitoring system configured to monitor for the release of the sensor gas from the gas emitter to determine erosion level of the system component; and
a controller configured to control the plasma processing system, further comprising:
a sensor gas source configured to provide a supply of said sensor gas; and
a gas supply line configured to connect said gas emitter to said sensor gas source in order to supply said sensor gas to said gas emitter.

50. A method of monitoring erosion of a system component in a plasma processing system, the method comprising:
providing the system component in plasma processing system, the system component having a first gas emitter at a first spatial location along an area of the system component, and a second gas emitter at a second spatial location along the area of the system component;
exposing the system component to a plasma process; and
monitoring the plasma processing system for a first sensor gas from the first gas emitter and a second sensor gas from the second gas emitter during the plasma process in order to determine erosion of the system component at the first and second spatial locations, wherein the first and second process gas are different from one another.

51. A monitorable consumable system component, comprising:
a system element that is consumed during processing performed by the system; a first gas emitter embedded within the system component at a first spatial location along an area of the system element; and
a second gas emitter embedded within the system element at a second spatial location along an area of the system component, wherein the first gas emitter contains a first sensor gas and the second gas emitter contains a second sensor gas different from the first sensor gas.

* * * * *